United States Patent
Kang et al.

(10) Patent No.: US 9,708,584 B2
(45) Date of Patent: Jul. 18, 2017

(54) MEDIUM COMPOSITION FOR REJUVENATING STEM CELLS

(71) Applicant: R. BIO CO., LTD., Seoul (KR)

(72) Inventors: Sung Keun Kang, Seoul (KR); Jeong Chan Ra, Suwon-si (KR); Hyeong Geun Park, Suwon-si (KR); Hang Young Lee, Suwon-si (KR)

(73) Assignee: R BIO CO., LTD., Seoul (KR)

( * ) Notice: Subject to any disclaimer, the term of this patent is extended or adjusted under 35 U.S.C. 154(b) by 0 days.

(21) Appl. No.: 14/360,621

(22) PCT Filed: Dec. 3, 2012

(86) PCT No.: PCT/KR2012/010380
§ 371 (c)(1),
(2) Date: May 25, 2014

(87) PCT Pub. No.: WO2013/081436
PCT Pub. Date: Jun. 6, 2013

(65) Prior Publication Data
US 2014/0322811 A1    Oct. 30, 2014

(30) Foreign Application Priority Data

Dec. 1, 2011   (KR) .................. 10-2011-0127885

(51) Int. Cl.
*C12N 5/077* (2010.01)
*C12N 5/0775* (2010.01)

(52) U.S. Cl.
CPC ........ *C12N 5/0667* (2013.01); *C12N 2500/90* (2013.01); *C12N 2501/11* (2013.01); *C12N 2501/115* (2013.01); *C12N 2501/33* (2013.01); *C12N 2501/39* (2013.01)

(58) Field of Classification Search
None
See application file for complete search history.

(56) References Cited

U.S. PATENT DOCUMENTS

| | | | |
|---|---|---|---|
| 6,900,051 B2 | 5/2005 | Kerr-Conte et al. | |
| 2007/0110729 A1 | 5/2007 | Kang et al. | |
| 2010/0233131 A1 | 9/2010 | Kang et al. | |
| 2012/0276064 A1* | 11/2012 | Blau ................. | A61K 31/7088 424/93.7 |

FOREIGN PATENT DOCUMENTS

| | | | | |
|---|---|---|---|---|
| CN | 101735980 A | 6/2010 | | |
| DE | WO 2010057614 A1 * | 5/2010 | ........... | C12N 5/0696 |
| KR | 100679642 B1 | 2/2007 | | |
| KR | 1020090108141 A | 10/2009 | | |
| WO | 0111011 A2 | 2/2001 | | |
| WO | 2007145438 A1 | 12/2007 | | |
| WO | 2008100083 A1 | 8/2008 | | |
| WO | 2010008219 A2 | 1/2010 | | |
| WO | 2012074265 A2 | 6/2012 | | |

OTHER PUBLICATIONS

Lin et al. "Accelerated growth and prolonged lifespan of adipose tissue-derived human mesenchymal stem cells in a medium using reduced calcium and antioxidants." Stem cells and Development 14(1): 92-102, 2005.*
Richard et al. "Polyunsaturated fatty acids as antioxidants", Pharmacological Research 57(6): 451-455, 2008.*
Iannitti et al. "Antioxidant therapy effectiveness: An up to date", European Review for Medical and Pharmacological Sciences 13: 1-34, 2009.*
CN 101735980 EPO translation.*
Ito, T., et al., "FGF-2 suppresses cellular senescence of human mesenchymal stem cells by down-regulation of TGF-beta2", "Biochemical and Biophysical Research Communications", May 21, 2007, pp. 108-114, vol. 359, No. 1.
Shibata, K., et al., "Expression of the p16INK4A Gene Is Associated Closely with Senescence of Human Mesenchymal Stem Cells and Is Potentially Silenced by DNA Methylation During In Vitro Expansion", "Stem Cells", Jun. 14, 2007, pp. 2371-2382, vol. 25, No. 9.
Zhang, X., et al., "Successful immortalization of mesenchymal progenitor cells derived from human placenta and the differentiation abilities of immortalized cells", "Biochemical and Biophysical Research Communications", Nov. 2, 2006, pp. 853-859, vol. 351, No. 4.

(Continued)

*Primary Examiner* — Emily Cordas
(74) *Attorney, Agent, or Firm* — Hulquist, PLLC; Steven J. Hultquist (57) ABSTRACT

The present invention relates to a medium composition for transforming stem cells from an aged person into young stem cells, and more particularly to a medium composition for culturing stem cells, which is used to rejuvenate stem cells from an aged person so as to have characteristics similar to those of the stem cells of young people, and to a method for rejuvenating stem cells, which comprises culturing stem cells from an aged person in the medium composition. According to the present invention, even mesenchymal stem cells collected from over 60 years old patients can be transformed into young mesenchymal stem cells having high differentiation ability, high telomerase activity, and high ability to express stem cell markers. Thus, the present invention can significantly increase the efficacy of cell therapy employing mesenchymal stem cells.

1 Claim, 12 Drawing Sheets

(56) References Cited

OTHER PUBLICATIONS

Blagosklonny, M., "Aging, Stem Cells, and Mammalian Target of Rapamycin: A Prospect of Pharmacologic Rejuvenation of Aging Stem Cells", "Rejuvenation Research", Jun. 5, 2008, pp. 801-808, vol. 11, No. 4.

Conboy, I., et al., "Rejuvination of Aged Progenitor Cells by Exposure to a Young Systemic Environment", "Nature", Feb. 17, 2005, pp. 760-764, vol. 433, No. 7927.

Lund, T., et al., "Mesenchymal Stem Cells from Donors Varying Widely in Age are of Equal Cellular Fitness After in vitro Expansion Under Hypoxic Conditions", "Cytotherapy", Jul. 6, 2010, pp. 971-981, vol. 12, No. 8.

Madonna, R., et al., "Enhanced Survival and Myocardin-A Induced Cariomyogenesis in Aged Mesenchymal Stem Cells Rejuvenated by Human Telomerase Gene Transfer", "Late-Breaking Basic Science Abstracts from the American Heart Association's Scientific Sessions 2011", "Circulation Research", Nov. 11, 2011, pp. e57-e58, vol. 109, No. 12, Abstract No. 26401.

Madonna, R., et al., "Mesenchymal Stem Cells Rejuvenation Afforded by Human Telomerase Gene Transfer Restored Myogenic Responses and Suppressed Fas-Mediated Apoptosis via Induction of Myocardin-A", "Cardiovascular Research Supplements", 2012, p. s40, vol. 93, No. 1.

Neupane, M., et al., "Isolation and Characterization of Canine Adipose-Derived Mesenchymal Stem Cells", "Tissue Engineering: Part A", 2008, pp. 1007-1015, vol. 14, No. 6.

Sun, Y., et al., "Rescuing Replication and Osteogenesis of Aged Mesenchymal Stem Cells by Exposure to a Young Extracellular Matrix", "The FASEB Journal", Jan. 6, 2011, pp. 1474-1485, vol. 25, No. 5.

Zheng, W., et al., "Loss of Proliferation and Differentiation Capacity of Aged Human Periodontal Ligament Stem Cells and Rejuvenation by Exposure to the Young Extrinsic Environment", "Tissue Engineering: Part A", Feb. 20, 2009, pp. 2263-2371, vol. 15, No. 9.

\* cited by examiner

CPDL by medium

Telomerase activity assay

| Medium age | 1 | 9 |
|---|---|---|
| 20 | 4.910 | 4.464 |
| 30 | 3.767 | 4.272 |
| 70 | 4.009 | 4.181 |
| 80 | 3.742 | 3.022 |

Fig. 7 telomerase activity: telomerase activity by subculture

| Medium Age | p4 M1 | p6 M1 | p4 M9 | p6 M9 |
|---|---|---|---|---|
| 20 | 4.910 | 2.307 | 4.464 | 2.591 |
| 30 | 3.767 | 3.016 | 4.272 | 3.329 |
| 70 | 4.609 | 1.672 | 4.181 | 1.520 |
| 80 | 3.742 | 1.750 | 3.022 | 1.120 |

Fig. 11 quantity

| Age\Medium | 1 | 2 | 3 | 9 | 10 |
|---|---|---|---|---|---|
| 20 | 0.3340 | 0.0985 | 0.2755 | 0.3338 | 0.1067 |
| 30 | 0.4857 | 0.1185 | 0.3677 | 0.4533 | 0.1090 |
| 70 | 0.2440 | 0.0962 | 0.2057 | 0.2405 | 0.1312 |
| 80 | 0.1658 | 0.0372 | 0.1690 | 0.1732 | 0.0490 |

## MEDIUM COMPOSITION FOR REJUVENATING STEM CELLS

CROSS-REFERENCE TO RELATED APPLICATIONS

This application is a U.S. national phase under 35 U.S.C. §371 of International Patent Application No. PCT/KR12/10380 filed Dec. 3, 2012, which in turn claims priority of Korean Patent Application No. 10-2011-0127885 filed Dec. 1, 2011. The disclosures of such international patent application and Korean priority patent application are hereby incorporated herein by reference in their respective entireties, for all purposes.

TECHNICAL FIELD

The present invention relates to a medium composition for transforming stem cells from an aged person into young stem cells, and more particularly to a medium composition for culturing stem cells, which is used to rejuvenate stem cells from an aged person so as to have characteristics similar to those of the stem cells of young people, and to a method for rejuvenating stem cells, which comprises culturing stem cells from an aged person in the medium composition.

BACKGROUND ART

Mesenchymal stem cells are pluripotent stem cells derived from various adult cells such as bond mallow cells, umbilical cord blood cells, placental cells (placental tissue cells) or adipose cells (or adipose tissue cells). For example, mesenchymal stem cells from bone marrow have pluripotency to differentiate into adipose tissue, bone/cartilage tissue and muscular tissue, and thus various studies on the development of cell therapeutic agents using mesenchymal stem cells have been conducted.

In recent years, as cell therapy technology utilizing mesenchymal stem cells has received attention, the development of the technology of activating mesenchymal stem cells from the human body so as to be suitable for therapeutic purposes has been required. Particularly, aged persons make up a significant portion of cell therapy patients, and mesenchymal stem cells collected from the tissue of an aged person have low therapeutic efficiency due to their low ability to proliferate and differentiate. In addition, technology of activating mesenchymal stem cells from an aged person to have characteristics similar to those of mesenchymal stem cells from young people has been required.

It is known that mesenchymal stem cells divide very slowly due to a senescence mechanism not associated with telomere shortening when being cultured in vitro, similar to other primary cultured human cells (Shibata, K. R. et al., *Stem cells*, 25; 2371-2382, 2007). This senescence mechanism has not yet been clearly found, but is known to occur mainly because environmental stress accumulates during long-term in vitro culture so that the Cdk inhibitory protein p16(INK4a) is expressed and accumulated to inhibit the activity of the Cdk protein that is involved in the growth of cells. It was found that, when the expression of the tumor gene Bmi-1 in mesenchymal stem cells was induced to inhibit the expression of p16, the senescence of the cells was inhibited (Zhang, X. et al. *Biochemical and biophysical research communications* 351; 853-859, 2006). In addition, it was reported that, when mesenchymal stem cells were treated with FGF-2 during culture to inhibit the mRNA expression of p21(Cip1), p53 and p16(INK4a), the arrest of growth of the mesenchymal stem cells in the G1 phase was inhibited (Ito, T. et al., *Biochemical and biophysical research communications,* 359; 108-114 2007). Moreover, Korean Patent Laid-Open Publication No. 10-2009-0108141 discloses a method of inhibiting the senescence of mesenchymal stem cells by transforming the mesenchymal stem cells with a gene encoding the Wip1 protein.

However, a method for rejuvenating aged mesenchymal stem cells collected from the tissue of an aged person has not yet been reported.

Accordingly, the present invention have found that, when mesenchymal stem cells collected from the adipose tissue isolated from an aged patient are cultured in a medium containing an antioxidant and a growth factor, mesenchymal stem cells having activity similar to that of the mesenchymal stem cells of young people can be produced, thereby completing the present invention.

DISCLOSURE OF INVENTION

It is an object of the present invention to provide a medium composition for rejuvenating mesenchymal stem cells from an aged person.

Another object of the present invention is to provide a method for rejuvenating mesenchymal stem cells, which comprises culturing mesenchymal stem cells from an aged person using the medium composition.

To achieve the above objects, the present invention provides a medium composition for rejuvenating mesenchymal stem cells from an aged person, the medium composition containing FBS (fetal bovine serum), an antioxidant, a cytokine, and NAC (N-acetyl-L-cysteine).

The present invention also provides a method for rejuvenating mesenchymal stem cells from an aged person, the method comprising culturing mesenchymal stem cells from an aged person in the above-described medium composition.

BEST MODE FOR CARRYING OUT THE INVENTION

In one aspect, the present invention is directed to a medium composition for rejuvenating mesenchymal stem cells from an aged person, the medium composition containing FBS (fetal bovine serum), an antioxidant, a cytokine, and NAC (N-acetyl-L-cysteine).

As used herein, the term "stem cells" refer to cells having not only self-replicating ability but also the ability to differentiate into at least two types of cells, and "adult stem cells" refer to stem cells that appear either in the stage in which each organ of an embryo is formed after the developmental process or in the adult stage.

As used herein, the term "mesenchymal stem cells" refers to undifferentiated stem cells isolated from the various tissues of humans or mammals. Particularly, mesenchymal stem cells in the present invention may be umbilical cord-derived mesenchymal stem cells, umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amnion-derived mesenchymal stem cells, and placenta-derived mesenchymal stem cells. Technology of isolating stem cells from each tissue is known in the art.

As used herein, the term "adipose-derived stem cells" refers to undifferentiated stem cells isolated from adipose tissue. For example, adipose-derived stem cells can be isolated in the following manner. Specifically, adipose-derived stem cells can be isolated by suspending adipose, obtained from liposuction, in physiological saline, culturing the suspension, treating the adipocyte layer, attached to the culture container such as a flask, with trypsin, and collecting the treated adipocytes, or collecting a small amount of the adipocytes, suspended in the physiological saline, using a scraper.

As used herein, the expression "rejuvenating stem cells" means making the phenotypes of mesenchymal stem cells from an aged people similar to the phenotypes of stem cells from young people. The phenotypes include the morphology of cells, the proliferation rate of cells, telomerase activity, the expression level of stem cell markers (Oct4, SSEA-1, Tra 1-60, Tra 1-81, Nanog etc.), and the ability of stem cells to differentiate. In the present invention, mesenchymal stem cells from an aged person are preferably cells isolated from a 60-120 year old person.

As used herein, the expression "making the phenotypes of mesenchymal stem cells from an aged people similar to the phenotypes of stem cells from young people" means either a state in which the phenotypes become more similar to those of stem cells from the tissue of young people compared to those in the first passage at which the mesenchymal stem cells from an aged people are isolated or a state in which the phenotypes become more similar to those of the stem cells of young people compared to those of mesenchymal stem cells cultured in media other than the culture medium of the present invention.

In the present invention, the medium composition may further contain insulin or an insulin-like factor and hydrocortisone, and the cytokine in the medium composition may be EGF (epidermal growth factor) and/or bFGF (basic fibroblast growth factor).

The antioxidant that is used in the medium composition of the present invention may be selenium, vitamin E, ascorbic acid, catechin, lycopene, beta-carotene, coenzyme Q-10, EPA (eicosapentaenoic acid), DHA (docosahexanoic acid) or the like. Preferably, the antioxidant may be selenium.

Thus, in the present invention, it was found that FBS, bFGF and EGF are essential factors for the culture of adipose stem cells from people of all age groups. Also, it was found that pluripotency, differentiation rate or telomerase activity was higher in cells from young people than in cells from aged people and that cells cultured in FBS-, bFGF- or EGF-free medium showed reduced growth rate, differentiation rate and telomerase activity, suggesting that FBS, bFGF and EGF are essential elements for the growth and activity of cells.

Moreover, in the present invention, it was found that cell differentiation rate of stem cell derived from young and aged group was similar between the selenium-free medium and selenium-containing control medium. However, the results of a telomerase activity assay between two media indicated that telomerase activity was lower in the aged-group cells cultured in selenium-free medium than in the young-group cells, suggesting that selenium should be essentially contained in a culture medium for cells from aged people to provide high telomerase activity.

In another aspect, the present invention is directed to a method for rejuvenating mesenchymal stem cells from an aged person, the method comprising culturing mesenchymal stem cells from an aged person in the above-described medium composition.

The basal medium that is used for culture of mesenchymal stem cells may be a conventional known in the art to be suitable for culture of stem cells, for example, DMEM, MEM or K-SFM medium. Preferably, it may be serum-free medium. Most preferably, it may be K-SFM (Keratinocyte-SFM; keratinocyte serum-free medium).

The medium that is used for culture of mesenchymal stem cells may be supplemented with additives known in the art to inhibit the differentiation of mesenchymal stem cells while promoting the proliferation of undifferentiated phenotypes thereof.

In addition, the medium may contain a neutral buffer (e.g., phosphate and/or high-concentration bicarbonate) in isotonic solution and a protein nutrient (e.g., serum such as FBS, serum replacement, albumin, or essential and nonessential amino acids such as glutamine). Furthermore, it may contain lipids (fatty acids, cholesterol, an HDL or LDL extract of serum) and other ingredients found in most stock media of this kind (e.g., insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

In addition, for the purpose of preventing cells from adhering to each other or to a vessel wall, or from forming large clusters, the medium may advantageously contain anti-clumping agents, for example, those sold by Invitrogen (Cat #0010057AE).

Among them, one or more additional additives selected from the following additives may advantageously be used:
stem cell factor (SCF, Steel factor), other ligands or antibodies that dimerize c-kit, and other activators of the same signal transduction pathway;
ligands for other tyrosine kinase related receptors, such as the receptor for platelet-derived growth factor (PDGF), macrophage colony-stimulating factor, Flt-3 ligand and vascular endothelial growth factor (VEGF);
factors that elevate cyclic AMP levels, such as forskolin;
factors that induce gp130, such as LIF or Oncostatin-M;
hematopoietic growth factors, such as thrombopoietin (TPO);
transforming growth factors, such as TGFβ1;
neurotrophins, such as CNTF.

The mesenchymal stem cells to be cultured according to the present invention can be obtained by, for example, the following method.

Human adipose tissue obtained from the abdomen by liposuction or the like is separated and washed with PBS. Then, the tissue is cut finely and degraded by collagenase-containing DMEM medium, after which it is washed with PBS and centrifuged at 1000 rpm for 5 minutes. The supernatant is removed, and the remaining pellets are washed with PBS and centrifuged at 1000 rpm for 5 minutes. The supernatant is removed through a 100 μm mesh filter, and the remaining cells are washed with PBS. Then, the cells are cultured overnight in DMEM medium (10% FBS, 2 mM NAC, 0.2 mM ascorbic acid), and after culture, the cells not attached to the culture container are washed with PBS and cultured in keratinocyte-SFM medium (containing NAC, ascorbic acid, calcium, rEGF, BPE, insulin and hydrocortisone) while the medium is replaced at 2-day intervals. Mesenchymal stem cells are separated from the medium and subcultured, thereby obtaining mesenchymal stem cells. In addition, mesenchymal stem cells can also be obtained by any method known in the art.

In one embodiment of the present invention, selenium is preferably used as an antioxidant in an amount of 0.5-1 ng/mL. If the content of selenium in the medium is less than 0.5 μg/l, the medium will be sensitive to oxygen toxicity, and if the content of selenium is more than 10 μg/l, it will cause serious cytotoxicity.

In the present invention, an insulin-like factor may be used as a substitute for insulin. It functions to enhance glucose metabolism and protein metabolism to promote cell growth. Preferably, recombinant IGF-1 (insulin-like growth factor-1) is used in the present invention. The content of the insulin-like factor in the medium is preferably 10-50 ng/ml. If the content of the insulin-like factor If the content of the insulin-like factor is less than 10 ng/ml, apoptosis will occur, and if the content of the insulin-like factor is more than 50 μg/l, it will cause cytotoxicity and increase the cost of the medium.

In addition, in an embodiment of the present invention, epidermal growth factor (EGF) is used in the medium. EGF can induce the proliferation of various types of cells in vivo and is preferably recombinant EGF. The content of EGF in the medium is preferably 10-50 ng/mL. If the content of EFG in the medium is less than 10 ng/mL, it will have no special effect, and if the content of EGF is more than 50 ng/mL, it will be cytotoxic.

In addition, in the present invention, basic fibroblast growth factor (bFGF) is used in the medium. It can induce the proliferation of various types of cells in vivo and is preferably recombinant bFGF. The content of bFGF in the medium is preferably 1-100 ng/mL.

In one example of the present invention, it could be found that FBS, bFGF and EGF are essential factors for the culture of adipose stem cells from people of all age groups. Particularly, it was found that a deficiency of bFGF has an important influence on the culture of adipose stem cells. In addition, it was found that the growth rate of cells increases as the age of people from which the cells are derived decreases.

In another example of the present invention, it was found that FBS, bFGF and EGF are important factors that determine the telomerase activity of adipose stem cells. Also, it could be seen that telomerase activity was the higher in cells from people in their 20s and that cells cultured in selenium-free medium had low telomerase activity. In addition, it was found that, when adipose stem cells from aged people were cultured in selenium-containing medium, they can have telomerase activity similar to that of adipose stem cells derived from young people.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation of Human Adipose Tissue-Derived Mesenchymal Stem Cells

Adipose tissue was isolated from abdomens of patients in their 20s, 30s, 70s and 80s by liposuction and washed with PBS. The washed adipose tissue was cut finely and degraded by DMEM media containing collagenase type1 (1 mg/ml) at 37° C. for 2 hours. The tissue treated with collagenase was washed with PBS, and then centrifuged at 1000 rpm for 5 minutes. The supernatant was removed, and then the remaining pellets were washed with PBS and centrifuged at 1000 rpm for 5 minutes. The centrifuged tissue was filtered through a 100 μm mesh filter to remove the supernatant, and then washed with PBS and cultured overnight in DMEM medium containing 10% FBS, 2 mM NAC (N-acetyl-L-cysteine) and 0.2 mM ascorbic acid.

Then, non-adherent cells were washed with PBS, and then subcultured in keratinocyte-SFM media (RKCM) containing 5% FBS, 2 mM NAC, 0.2 mM ascorbic acid, 0.09 mM calcium, 5 ng/ml rEGF, 5 μg/ml insulin, 10 ng/mL bFGF, 74 ng/ml hydrocortisone and 1 ng/ml selenium while the medium was replaced at 2-day intervals. After the cells were subcultured three times, the activity of the adipose stem cells from people in their 20s, 40s and 70s was analyzed.

To analyze the activity of the stem cells, the microscopic morphology, differentiation marker, telomerase activity, telomere length and differentiation ability of the stem cells were measured.

As a result, it was found that the adipose stem cells isolated from people in their 20s, 40s and 70s had similar activities after they were subcultured three times.

Example 2

Determination of Medium Components that Rejuvenate Stem Cells

Media free of one of FBS, NAC, ascorbic acid, calcium, rEGF, 5 µg/ml insulin, bFGF, hydrocortisone and selenium, which are the active components added to the RKCM media used in Example 1, were prepared. Also, the phenotypes of adipose stem cells from patients in their 20s, 30s, 70s and 80s in the media free of each of the active components were analyzed.

Medium Nos. 1 to 10 were prepared. Medium No. 1 was RKCM medium, and medium Nos. 2 to 10 were media free of each of the active ingredients in the RKCM medium. The active components absent in the media are shown in Table 1 below.

TABLE 1

| Media No. | Active components absent in RKCM media |
|---|---|
| 1 | No |
| 2 | FBS |
| 3 | bFGF |
| 4 | Insulin |
| 5 | Hydrocortisone |
| 6 | EGF |
| 7 | ascorbic acid |
| 8 | NAC(N-acetyl-L-cysteine) |
| 9 | Selenium |
| 10 | EGF/bFGF |

(1) Observation of Morphology and Proliferation Rate

Figure 1:
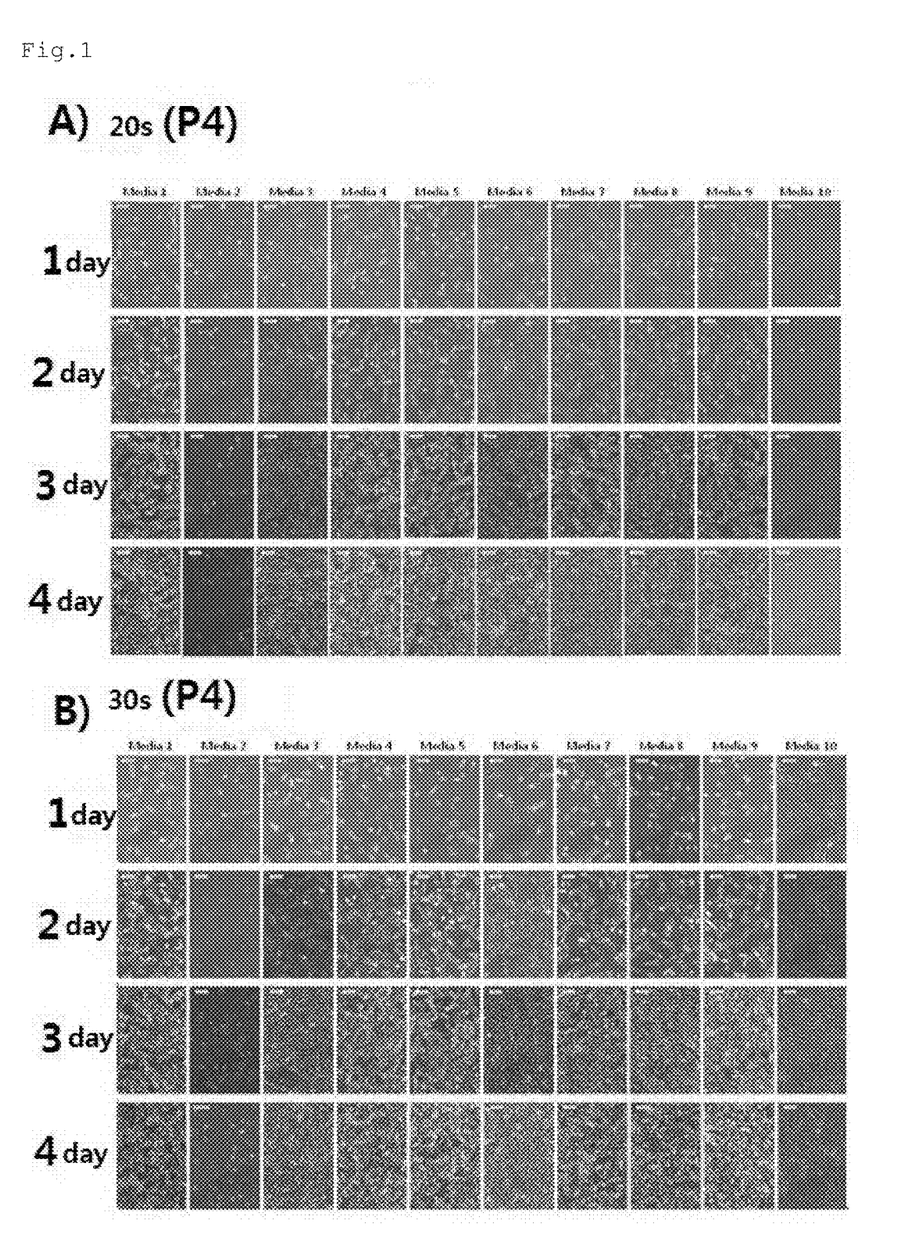
FIG. 1 shows micrographs of adipose stem cells from persons in their 20s and 30s, subcultured in each medium to passage 4.
Figure 2:
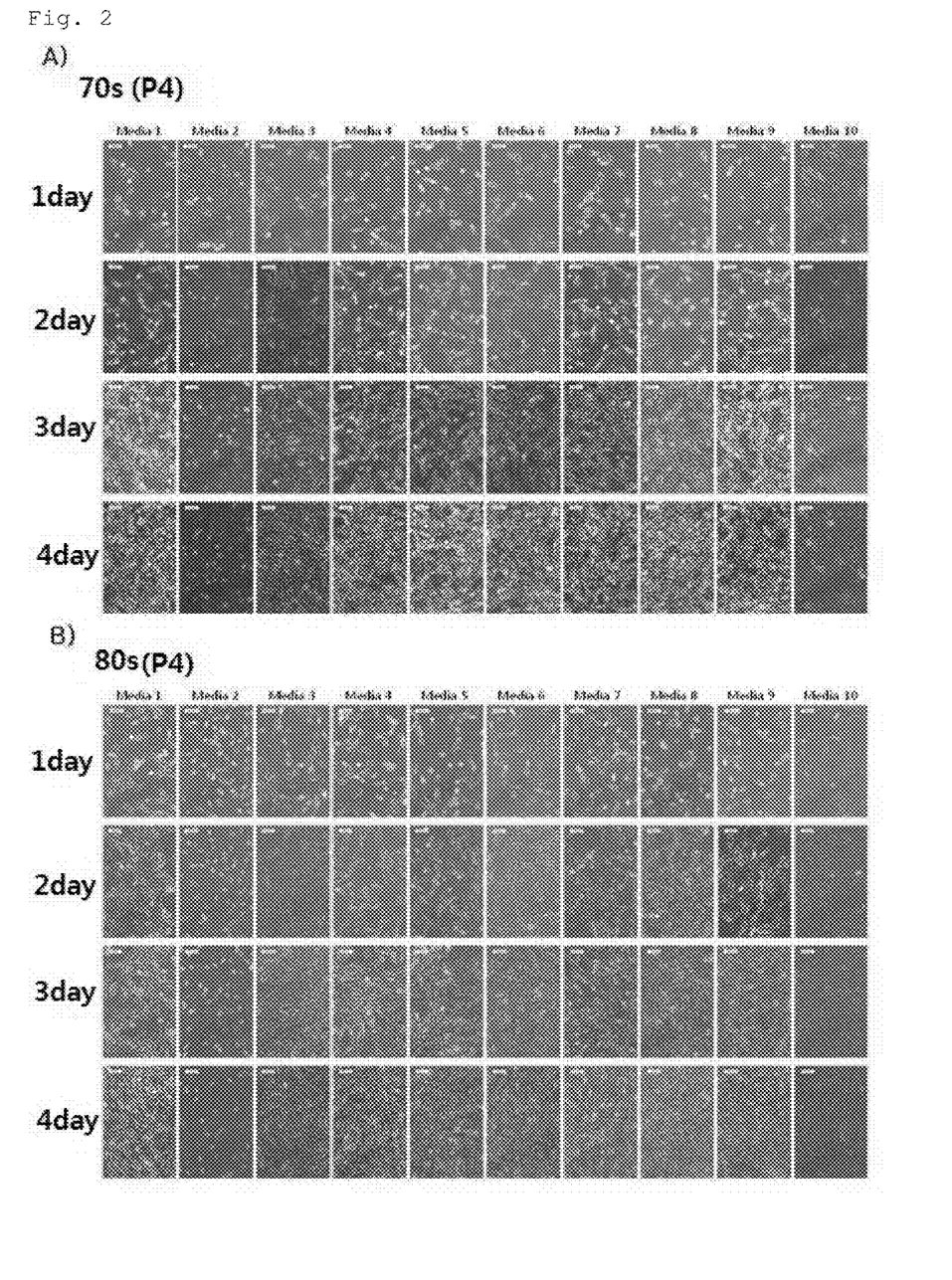
FIG. 2 shows micrographs of adipose stem cells from persons in their 70s and 80s, subcultured in their media to passage 4.

The adipose stem cells isolated from patients in their 20s, 30s, 70s and 80s by the method of Example 1 were subcultured to passage 4, and their morphology was observed with a microscope (FIGS. 1 and 2). Also, the number of the cells in each subculture process was measured with a hemocytometer to determine the proliferation rate of the cells.

Figure 3:
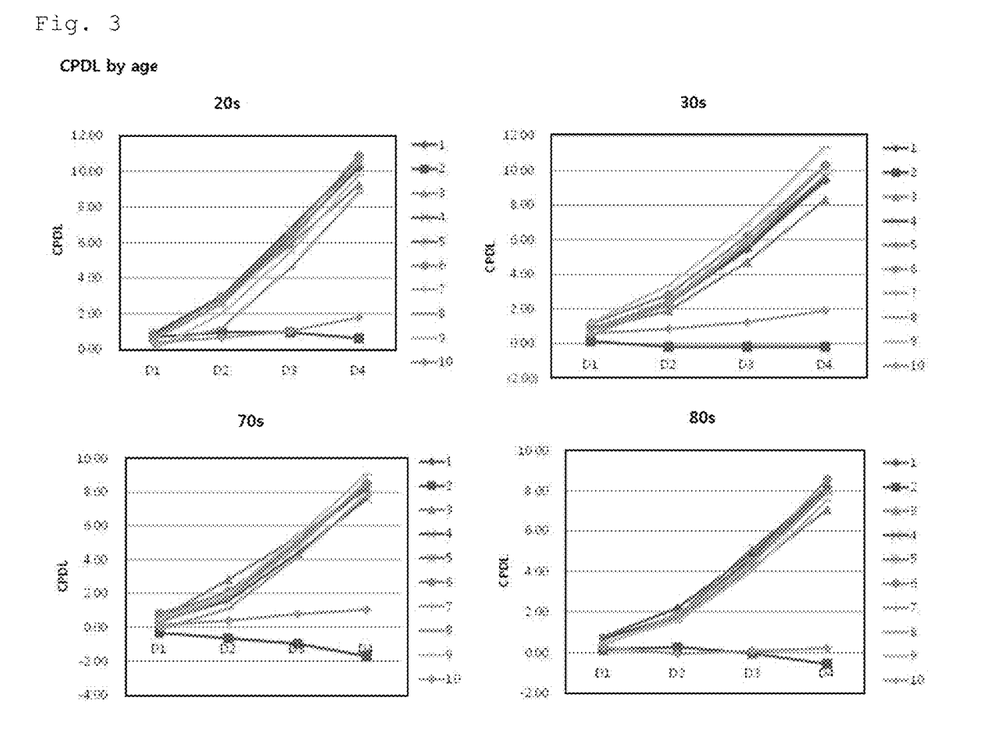
FIG. 3 is a graphic diagram showing the cell population doubling levels (CPDLs) of cells from young people (in their 20s and 30s) and aged people (in their 70s and 80s), cultured in 10 different media.
Figure 4:
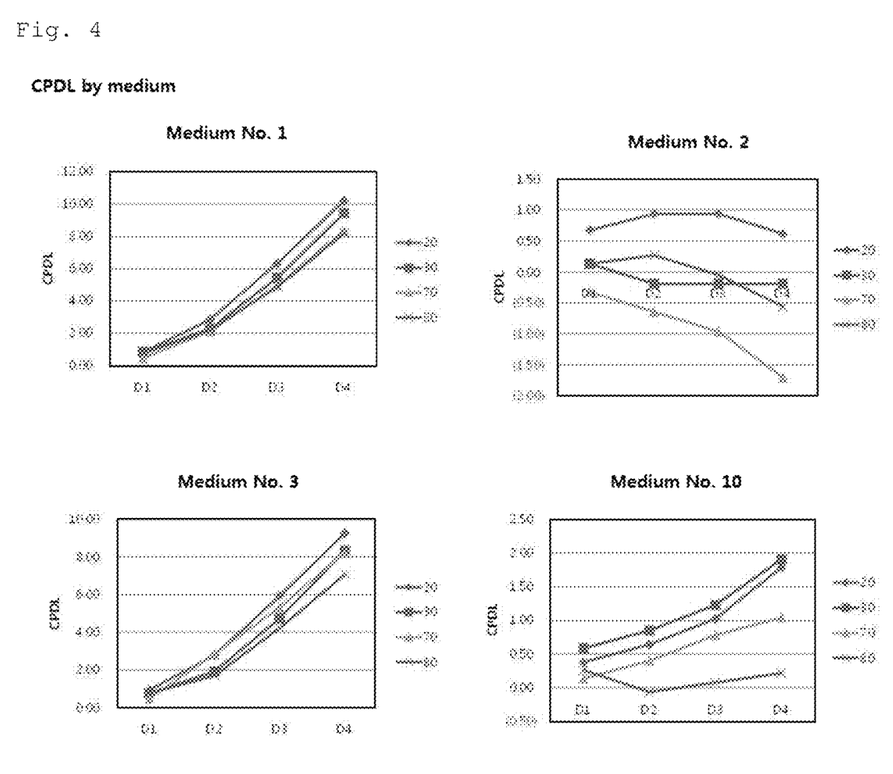
FIG. 4 is a graphic diagram showing the cell population doubling levels (CPDLs) of cells from young people (in their 20s and 30s) and aged people (in their 70s and 80s), cultured in various media.

FIGS. 3 and 4 show the cell population doubling levels (CPDLs) of the cells from young people (in their 20s and 30s) and from aged people (in their 70s and 80s), cultured in the 10 different media, and show the CPDLs according to age and medium, respectively. As can be seen therein, the CPDLs of the adipose mesenchymal stem cells from young people (in their 20s and 30s) and from aged people (in their 70s and 80s), cultured in the 10 different media from each of the 10 active components, were higher in the order of 20s, 30s, 70s and 80s of age, except for medium Nos. 2 and 10. The growth rate of the cell did slightly differ among the media and was the highest in medium No. 1, 6 or 7 and the lowest in medium No. 2.

The morphology or growth rate of the adipose stem cells cultured in the 10 different media was observed, and as a result, it could be seen that the components absent in medium Nos. 2, 3 and 10 are essential factors in the culturing of adipose mesenchymal stem cells from people of all age groups and that the component absent in medium No. 3 has a more important influence on the culturing of adipose mesenchymal stem cells compared to the components absent in medium Nos. 2 and 10. In addition, it was found that the growth rate of the cells increases as the age of people from which the cells were derived decreases.

(2) Analysis of Telomerase Activity

The adipose stem cells isolated from patients in their 20s, 30s, 70s and 80s by the method of Example 1 were subcultured in five different media (Nos. 1, 2, 3, 9 and 10) to passage 3, and then the telomerase activities of the cells were analyzed.

The adipose-derived mesenchymal stem cells cultured in the media were washed with PBS, and then digested with collagenase-containing DMEM medium at 37° C. for 2 hours. Then, the cells were washed with PBS, and then centrifuged at 3000×g for 10 minutes. The supernatant was removed, and the remaining cells were lysed with a lysis buffer in Telo TAGGG Telomerase PCR ELISA kit (Roche) and allowed to stand on ice for 30 minutes. The cell lysate was centrifuged at 16,000×g for 20 minutes, and a portion of the supernatant was mixed with a reaction mixture contained in the kit and subjected to a PCR reaction under the following conditions: elongation at 25° C. for 10 min, inactivation at 94° C. for 5 min, denaturation at 94° C. for 30 sec, annealing at 50° C. for 30 sec, and polymerization at 72° C. for 90 sec. 5 µl of the PCR amplified sample was allowed to react with 25 µl of a denaturation reagent, contained in the kit, at room temperature for 10 minutes, and then mixed with 225 µl of a hybridization solution. 100 µl of the mixture was dispensed onto a coated microplate and allowed to react at 37° C. for 2 hours at a speed of 300 rpm, and then the hybridization solution was removed. The resulting material was washed several times with washing buffer, and then 100 µl of anti-DIG-POD solution was added thereto and allowed to react at room temperature at a speed of 300 rpm for 30 minutes. Then, the solution was removed, and the remaining material was washed several times with washing buffer. 100 µl of TMB substrate solution was added thereto and allowed to react at room temperature at a speed of 300 rpm for 30 minutes. Then, 100 µl of a stop solution was added thereto and a change in the color of the mixture was observed. When the stop solution was added, the color changed from blue to yellow, and within 30 minutes, the absorbance at a wavelength of 450 nm was measured with a microplate (ELISA) device.

Figure 5:
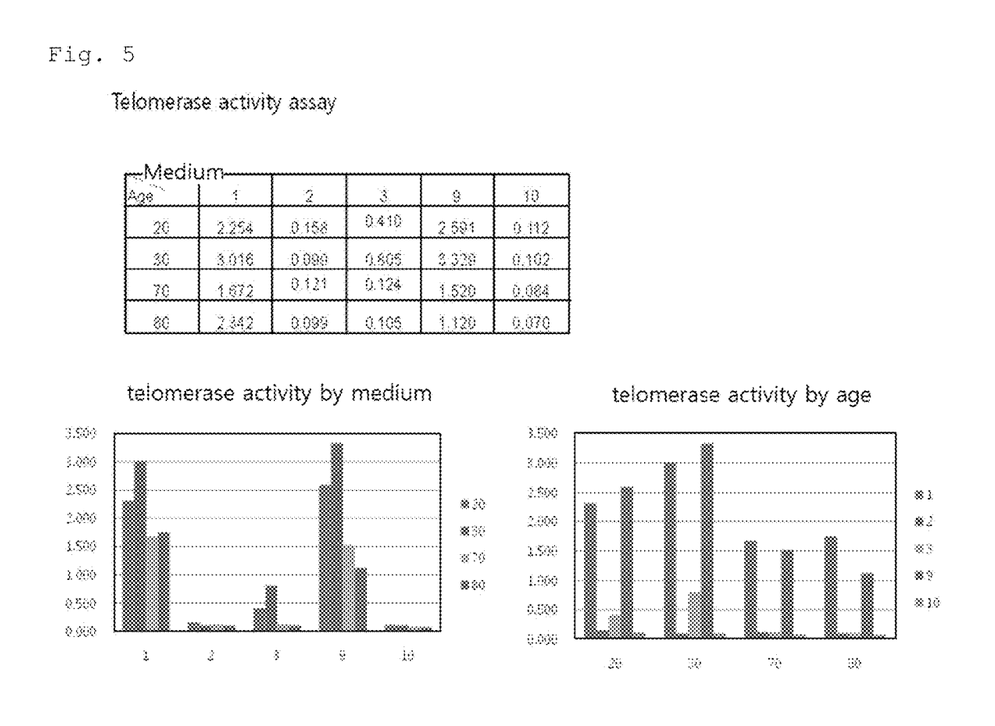
FIG. 5 is a graphic diagram showing the telomerase activities of adipose stem cells, derived from people with various ages and cultured in five different media.

As a result, as shown in FIG. 5, the telomerase activity of the adipose stem cells cultured in the five different media was the highest in medium No. 9 in the case of the cells from people in their 20s or 30s, and the cells in medium Nos. 2, 3 and 10 had little or no telomerase activity. In the case of the cells from aged people, the cells cultured in medium No. 1 showed activity slightly higher than those cultured in medium No. 9. Also, in the case of the cells from aged people, the telomerase activities of the cells cultured in medium Nos. 2, 3 and 10 were low.

Figure 6:
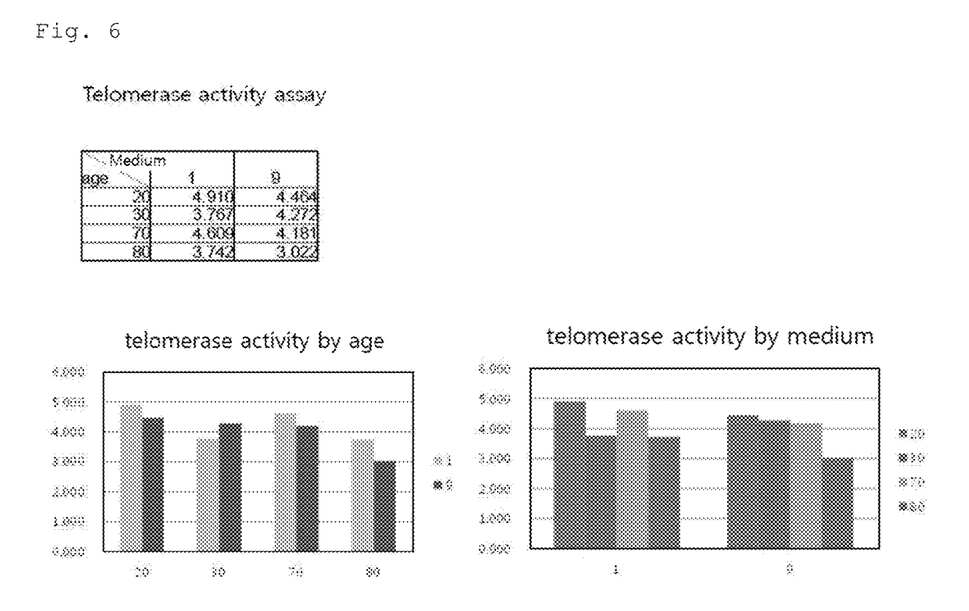
FIG. 6 is a graphic diagram showing the telomerase activities of adipose stem cells from people in their 20s, 30s, 70s and 80s, cultured in two different media (medium Nos. 1 and 9).

FIG. 6 shows the telomerase activities of the cells from people in their 20s, 30s, 70s and 80s, cultured in two different media (medium Nos. 1 and 9).

As a result, the telomerase activities of the adipose stem cells cultured in medium Nos. 1 and 9 were the highest in the cells from people in their 20s and were higher in the cells cultured in medium No. 1 than in the cells cultured in medium No. 9, except for the cells from people in their 30s.

In addition, when the cells were cultured in medium Nos. 1 and 9 to passage P4, the pluripotency of the cultured cells was the highest in the cells from people in their 80s, whereas the telomerase activity was the highest in the cells from people in their 20s. Based on only the results of analysis of telomerase activity, it can be seen that the component absent in medium No. 9 more reduces the activity of stem cells compared to the component absent in medium No. 1, even though the difference is insignificant. In addition, it was found that, when cells from aged people are cultured in a medium containing the component absent in medium No. 9, the cells can have activity similar to that of cells from young people, suggesting that the component is an important component.

Additionally, cells were cultured in medium Nos. 1 and 9 to passage P4 and passage P6, and then the change in telomerase activity with the number of subculture passages was measured.

Figure 7:
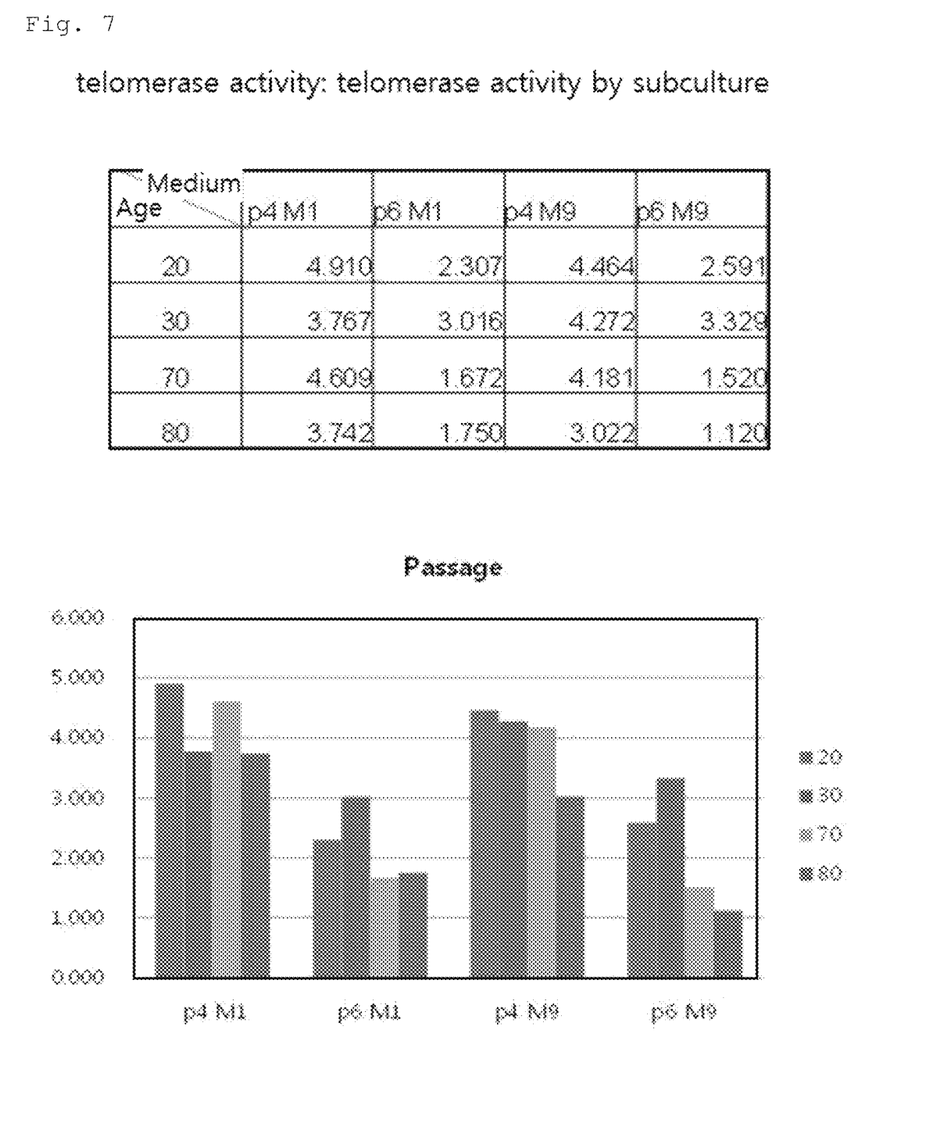
FIG. 7 is a graphic diagram showing the results of measuring the change in telomerase activity with the number of subcultures after culturing cells to passage P4 and passage P6 using medium Nos. 1 and 9.

As a result, as can be seen in FIG. 7, telomerase activity was higher in passage P4 than in passage P6 in all age groups and the two media.

(3) Analysis of Expression of Stem Cell Marker

The adipose stem cells isolated from people in their 20s, 30s, 70s and 80s by the method of Example 1 were subcultured in medium Nos. 1 and 9 to passage 3, and then grown to a confluence of 90%. After removing the media, the grown adipose stem cells were washed one or more times with PBS, and then lysed with lysis buffer (Intron Biotechnolgy, Sungnam, Korea) for RNA extraction, and RNA was extracted from the cells using a total extraction kit (Intron Biotechnolgy). The extracted RNA was converted into cDNA (Intron Biotechnology cDNA syntheis kit), which was then subjected to PCR using constructed primers for the pluripotency markers oct-4, Nanog and Rex1. The PCR products were electrophoresed, and then quantified by an image analyzer.

Figure 8:
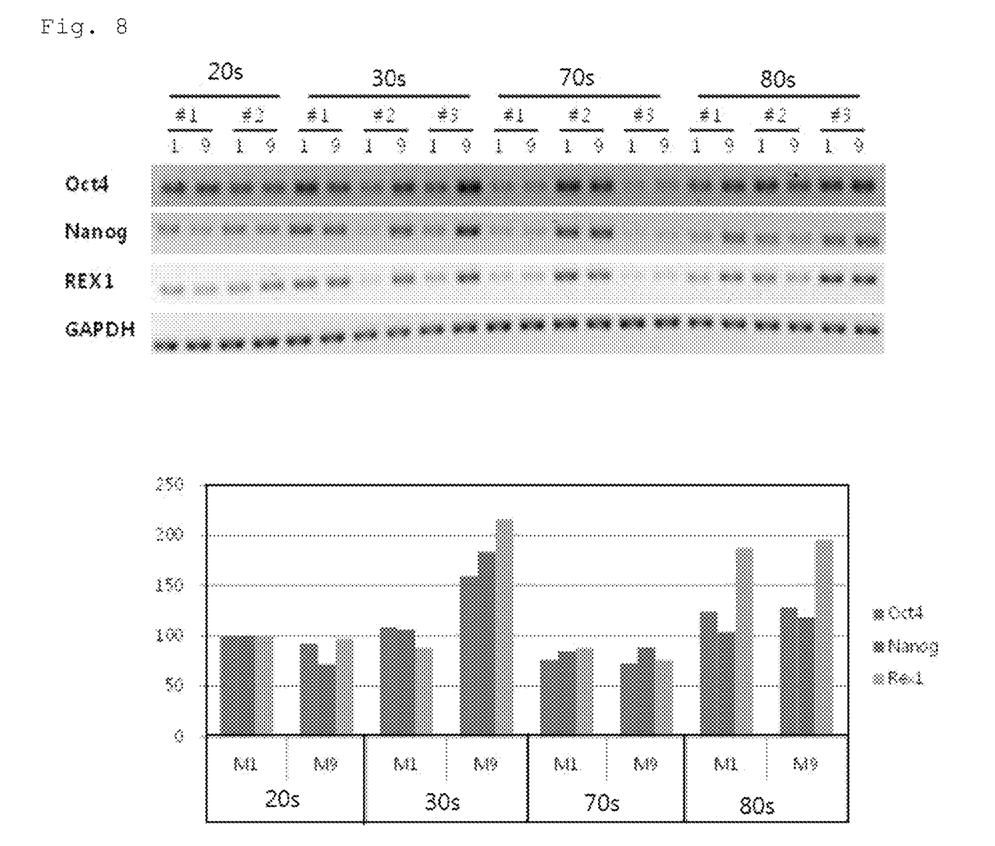
FIG. 8 shows the results of measuring the expression levels of the pluripotency markers oct4, nanog and Rex1 in adipose stem cells cultured in medium Nos. 1 and 9 to P3.

As a result, as can be seen in FIG. 8, the adipose stem cells cultured in medium Nos. 1 and 9 all showed the pluripotency markers oct4, nanog and Rex1, even though the difference in the expression of the markers between the stem cells was significant. The expression level of the markers was higher in the cells from people in their 80s than in the cells from other age groups. Also, the expression level was higher in medium No. 9 than in medium No. 1 in the case of only the cells from people in their 30s, and the other age groups showed similar marker expression levels.

Figure 9:
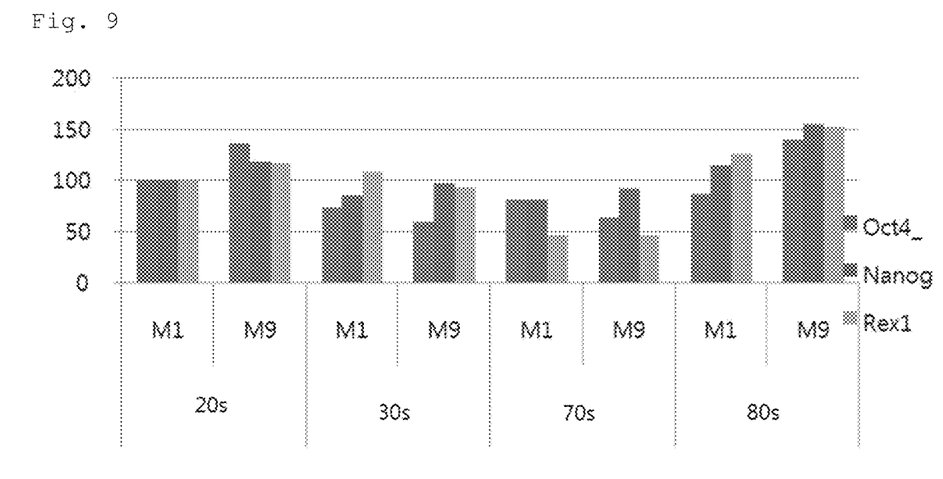
FIG. 9 shows the results of measuring the expression levels of the pluripotency markers oct4, nanog and Rex1 in adipose stem cells cultured in medium Nos. 1 and 9 to passage P4.

In addition, the adipose mesenchymal stem cells cultured in medium Nos. 1 and 9 expressed the pluripotency markers oct4, nanog and Rex1, even though the expression level of the markers was significant between the stem cells (FIG. 9). The expression levels of the markers was higher in the cells from people in their 80s than in the cells from other age groups and was higher in medium No. 9 than in medium No. 1 in the case of all age groups.

(4) Analysis of Differentiation Ability

The adipose stem cells isolated from people in their 20s, 30s, 70s and 80s by the method of Example 1 were subcultured in five different media (Nos. 1, 2, 3, 9 and 10), and then cultured in NH Adipodiff medium (adipose differentiation medium) (Miltenyi Biotec, Bergisch Gladbach, Germany) under the conditions of 37° C. and 5% $CO_2$ for 21 days while the adipose differentiation medium was replaced at 2-day intervals. 21 days after the start of culture in the adipose differentiation medium, the ability of the adipose stem cells to differentiate into adipocytes was analyzed by oil red O staining.

Figure 10:
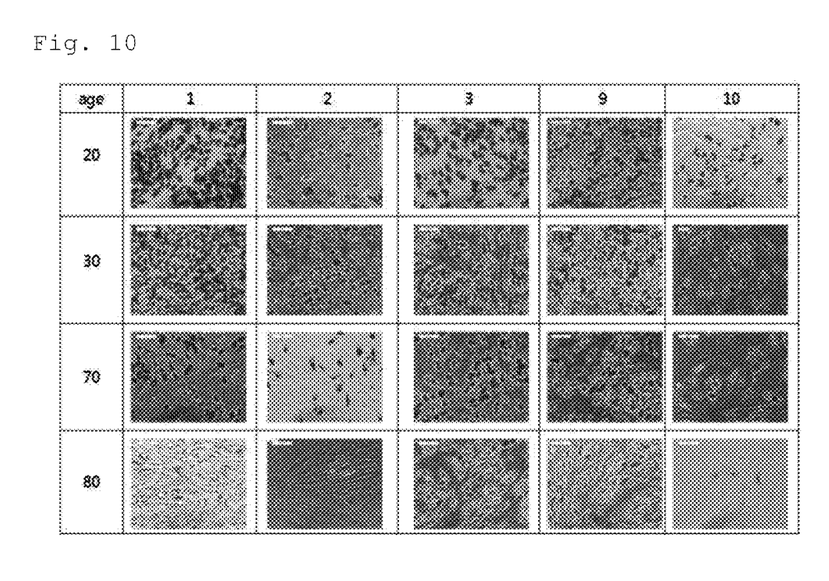
FIG. 10 shows samples for subjects aged 20, 30, 70, and 80, in which a lipid drop (the characteristic of adipose differentiation) together with oil red O staining was observed in the cells, as derived from all age groups and cultured in all the media.
Figure 11:
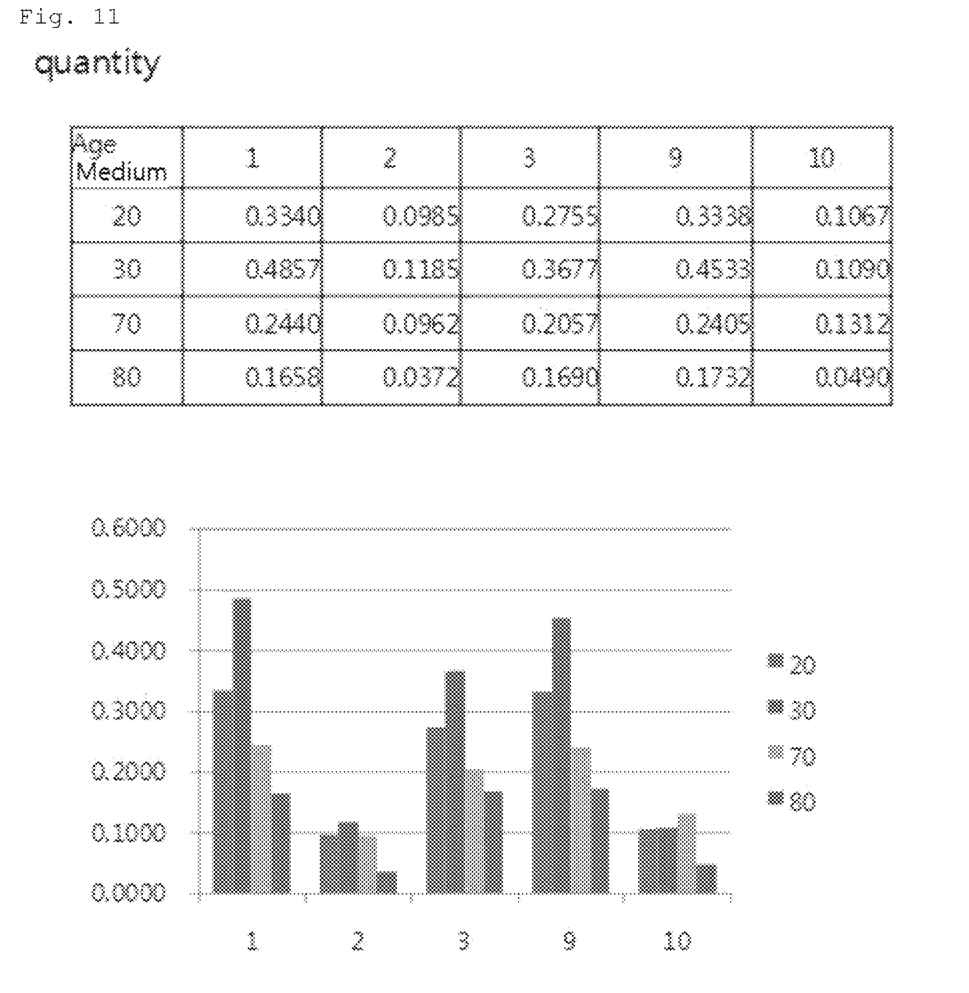
FIG. 11 is a tabulation and graph showing the results of quantifying the adipose differentiation for the samples of FIG. 10.

As a result, as shown in FIG. 10, a lipid drop (the characteristic of adipose differentiation) together with oil red O staining was observed in the cells, which were derived from all age groups and cultured in all the media. FIG. 11 shows the results of quantifying the adipose differentiation. As can be seen therein, the differentiation rate was higher in the order of medium Nos. 9, 1 and 3 and was similar between medium Nos. 2 and 10. Also, the differentiation rate was higher in the order of 30s, 20s, 70s and 80s of age.

Figure 12:
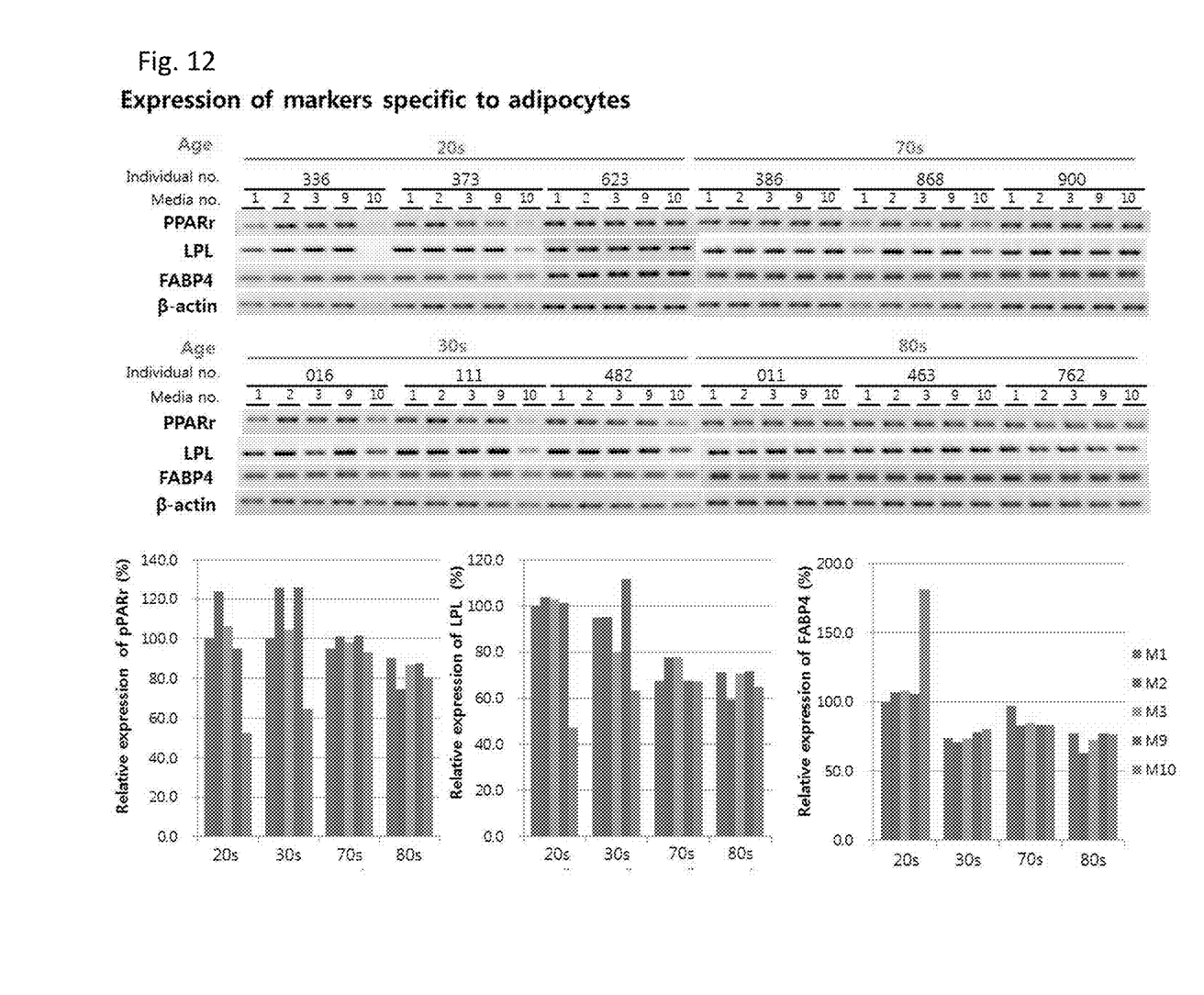
FIG. 12 shows the results for expression levels of adipose differentiation markers specific to adipocytes, for markers PPARr, LPL, and FABP4d analyzed by RT-PCR, for subjects in their 20s, 30s, 70s, and 80s.

The expression levels of the adipose differentiation markers PPARr, LPL and FABP4d were analyzed by RT-PCR at the molecular level. As a result, as shown in FIG. 12, the expression level was slightly higher in the young age group than in the aged group, even though the difference in the expression level between the individuals was significant. Also, the expression level was similar between the media or was slightly higher in medium Nos. 2 and 9.

From the above-described results, it was found that the active components absent in medium Nos. 2, 3 and 10 are essential factors for the culture of adipose mesenchymal stem cells from people of all age groups. Also, it was found that pluripotency, differentiation rate or telomerase activity was higher in cells from young people than in cells from aged people and that cells cultured in medium Nos. 2, 3 and 10 showed reduced growth rate, differentiation rate and telomerase activity, suggesting that the components absent in these media are essential elements for the growth and activity of cells.

Moreover, it was found that the cell differentiation rate in medium No. 9 free of selenium was similar between the young group and the aged group, but the results of the telomerase activity assay between two media indicated that telomerase activity was lower in the aged-group cells cultured in selenium-free medium No. 9 than in the young-group cells, suggesting that selenium absent in medium No. 9 should be essentially contained in a culture medium for the cells from aged people in order to provide telomerase activity similar to that of the cells cultured in medium No. 1.

INDUSTRIAL APPLICABILITY

According to the present invention, even mesenchymal stem cells collected from over 60 years old patients can be transformed into young mesenchymal stem cells having high differentiation ability, high telomerase activity, and high ability to express stem cell markers. Thus, the present invention can significantly increase the efficacy of cell therapy employing mesenchymal stem cells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for rejuvenating mesenchymal stem cells from an aged person, the method comprising:
  culturing mesenchymal stem cells from an aged person in a medium composition containing FBS (fetal bovine serum), 0.5-1 ng/ml selenium, NAC (N-acetyl-L-cysteine), 10-50 ng/ml EGF (epidermal growth factor), 1-100 ng/ml bFGF (basic fibroblast growth factor), insulin or insulin-like factor, and hydrocortisone,
  wherein the aged person is a 60-120 year old person,
  wherein said rejuvenating is one or more of the following characteristics:
    (i) promoting proliferation rate;
    (ii) increasing of telomerase activity;
    (iii) increasing of pluripotency markers expression level; and
    (iv) increasing of differentiation ability.

* * * * *

UNITED STATES PATENT AND TRADEMARK OFFICE
CERTIFICATE OF CORRECTION

| | |
|---|---|
| PATENT NO. | : 9,708,584 B2 |
| APPLICATION NO. | : 14/360621 |
| DATED | : July 18, 2017 |
| INVENTOR(S) | : Sung Keun Kang et al. |

Page 1 of 1

It is certified that error appears in the above-identified patent and that said Letters Patent is hereby corrected as shown below:

On the Title Page

Applicant item (71): "R. BIO CO., LTD." should be --R BIO CO., LTD.--.

Attorney, Agent, or Firm item (74): "Hulquist, PLLC" should be --Hultquist, PLLC--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*